US00PP27418P2

(12) United States Plant Patent
Saul

(10) Patent No.: US PP27,418 P2
(45) Date of Patent: Nov. 22, 2016

(54) ***KNIPHOFIA* PLANT NAMED 'ECHO YELLO'**

(50) Latin Name: *Kniphofia uvaria*
Varietal Denomination: Echo Yello

(71) Applicant: Richard Gregg Saul, Cleveland, GA (US)

(72) Inventor: Richard Gregg Saul, Cleveland, GA (US)

(73) Assignee: ITSAUL PLANTS LLC, Alpharetta, GA (US)

( * ) Notice: Subject to any disclaimer, the term of this patent is extended or adjusted under 35 U.S.C. 154(b) by 91 days.

(21) Appl. No.: 14/545,055

(22) Filed: Mar. 20, 2015

(51) Int. Cl.
*A01H 5/02* (2006.01)

(52) U.S. Cl.
USPC ..... Plt./443

(58) Field of Classification Search
USPC ..... Plt./443
See application file for complete search history.

*Primary Examiner* — Keith Robinson
(74) *Attorney, Agent, or Firm* — Penny J. Aguirre

(57) ABSTRACT

A new cultivar of *Kniphofia*, 'Echo Yello', that is characterized by its exhibits full racemes an average of 16 cm in height that stand above the foliage with flowers that are clear citron yellow in color, its floriferous and early blooming habit that commences in mid spring and re-blooms into the fall in Georgia, its sturdy flowering stems reaching 76 cm in height in the spring and 61 cm in height during the summer over foliage that reaches up to 56 cm in height and 72 cm in width, its tight crowns of multiple shoots when finished in a trade one-gallon container, and its foliage that is light to medium green in color.

2 Drawing Sheets

Botanical classification: *Kniphofia uvaria.*
Varietal denomination: 'Echo Yello'.

BACKGROUND OF THE INVENTION

The present invention relates to a new and distinct cultivar of *Kniphofia uvaria* and will be referred to hereafter by its cultivar name, 'Echo Yello'. 'Echo Yello' is a new cultivar of red hot poker or torch lily, a perennial plant grown for landscape use.

The new cultivar was derived from a controlled breeding program conducted by the Inventor at his nursery in Dahlonega, Ga., USA. The overall purpose of the breeding program is to make selections of *Kniphofia* with unique flower colors combined with a re-blooming habit. 'Echo Yello' originated as a seedling that arose from seed planted from the open pollinated plants of *Kniphofia* 'Echo Mango' (U.S. Plant Pat. No. 21,706) in spring of 2009. 'Echo Yello' was selected as a single unique plant from amongst the resulting seedlings in summer of 2011. The male parent is unknown.

Asexual propagation of the new cultivar was first accomplished by division by the Inventor in Dahlonega, Ga. in summer of 2011. Asexual propagation by division and in vitro propagation has determined that the characteristics of the new cultivar are stable and are reproduced true to type in successive generations.

SUMMARY OF THE INVENTION

The following traits have been repeatedly observed and represent the characteristics of the new cultivar of *Kniphofia*. These attributes in combination distinguish 'Echo Yello' as a unique cultivar of *Kniphofia.*

1. 'Echo Yello' exhibits full racemes an average of 16 cm in height that stand above the foliage with flowers that are clear citron yellow in color.
2. 'Echo Yello' exhibits a floriferous and early blooming habit that commences in spring and re-blooms into the fall in Georgia.
3. 'Echo Yello' exhibits sturdy flowering stems reaching 76 cm in height in the spring and 61 cm in height during the summer over foliage that reaches up to 56 cm in height and 72 cm in width.
4. 'Echo Yello' exhibits tight crowns of multiple shoots when finished in a trade one-gallon container.
5. 'Echo Yello' exhibits foliage that is light to medium green in color.

The female parent of 'Echo Yello', 'Echo Mango', is similar to 'Echo Yello' in overall plant habit and in having a floriferous and re-blooming plant habit. 'Echo Mango', differs from 'Echo Yello' in having flowers that are apricot in color. 'Echo Yello' can be most closely compared to the *Kniphofia* cultivars, 'Echo Rojo' (U.S. Plant Pat. No. 22,791) and 'Lemon Popsicle' (U.S. Plant Pat. No. 24,011). 'Echo Rojo' is similar to 'Echo Yello' in having a re-blooming bloom habit. 'Echo Rojo' differs from 'Echo Yello' in having flowers that are orange-red in color, in having a later commencing and less floriferous blooming habit and in producing less new shoots during production. 'Lemon Popsicle' is similar to 'Echo Yello' in having yellow flowers and a re-blooming habit. 'Lemon Popsicle' differs from 'Echo Yello' in having inflorescences that are shorter in length with fewer individual flowers, in having flowers that are held perpendicular to the stem, and in having inflorescences that are more rounded in shape as they mature.

BRIEF DESCRIPTION OF THE DRAWINGS

The accompanying colored photographs illustrate the overall appearance and distinct characteristics of the new

*Kniphofia*. The photographs were taken of a one year-old plant as grown outdoors in a cold frame in in Alpharetta, Ga.

Figure 1:
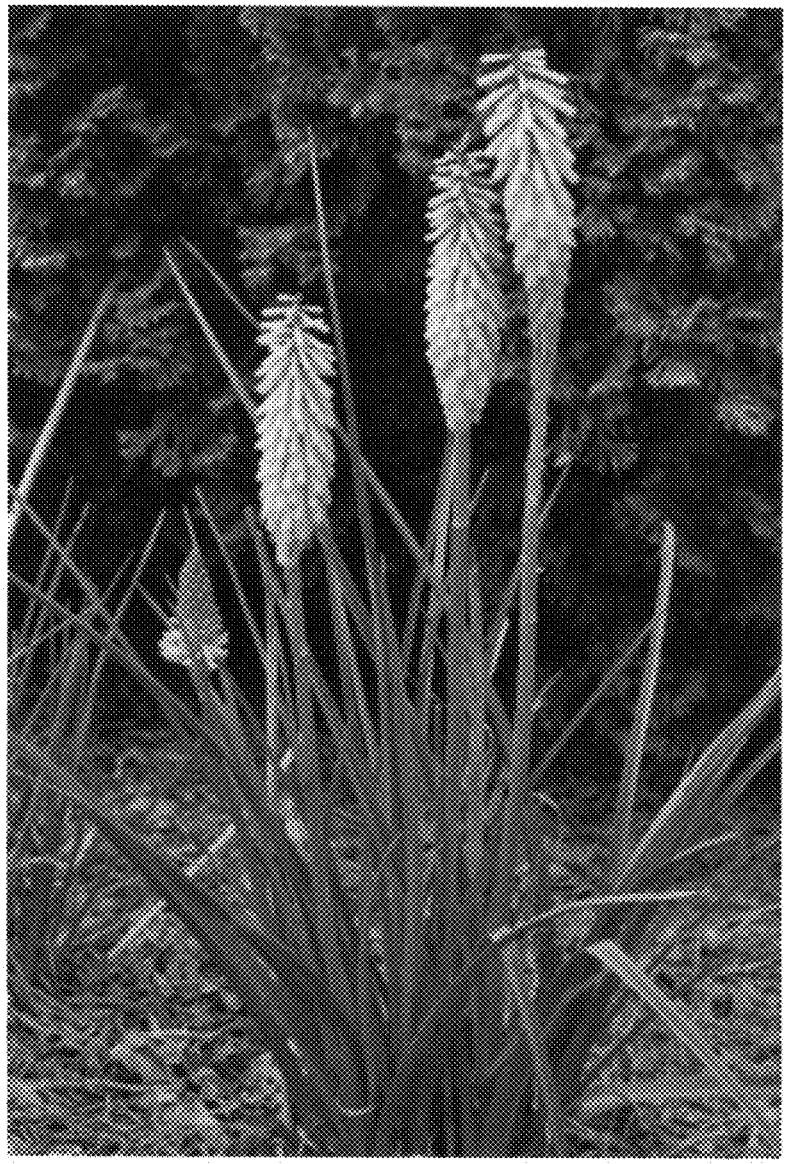

The photograph in FIG. 1 provides a side view of the overall habit and appearance of 'Echo Yello' in bloom.

Figure 2:
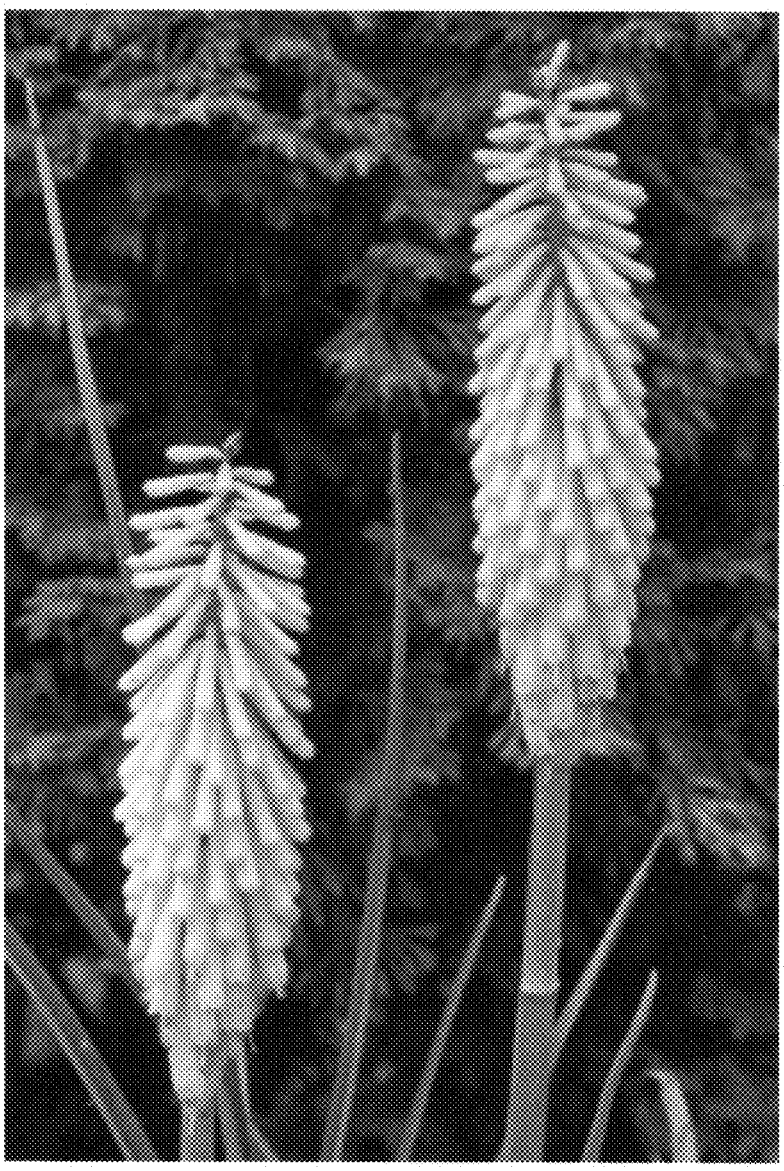

The photograph in FIG. 2 provides a close-up view of the inflorescences of 'Echo Yello'.

The colors in the photographs are as close as possible with the digital photography techniques available, the color values cited in the detailed botanical description accurately describe the colors of the new *Kniphofia*.

DETAILED BOTANICAL DESCRIPTION

The following is a detailed description of plants of the new cultivar one year-old plants as grown in one-gallon containers outdoors in a cold frame and forced into bloom under daylight extension in Alpharetta, Ga. The phenotype of the new cultivar may vary with variations in environmental, climatic, and cultural conditions, as it has not been tested under all possible environmental conditions. The color determinations are in accordance with The 2007 R.H.S. Colour Chart of The Royal Horticultural Society, London, England, except where general color terms of ordinary dictionary significance are used.

General description:

*Blooming habit*.—Begins blooming in late April to early May and continues into the fall in Georgia.

*Plant type*.—Herbaceous perennial.

*Plant habit*.—Clump-forming habit with upright to arching basal grass-like leaves and sturdy, upright flowers stems with blooms above the foliage.

*Height and spread*.—Foliage reaches up to 56 cm in height and 72 cm in spread (about 11 cm at base) with flowering stems reaching up to 76 cm in height.

*Hardiness*.—At least in U.S.D.A. Zones 6 to 9.

*Diseases and pests*.—No susceptibility and resistance to diseases and pests has been observed.

*Root description*.—Fleshy and thick.

*Propagation*.—In vitro propagation (preferred) or division.

*Time required for root development*.—A 72 cell plug from tissue culture roots out a trade gallon pot in about 6 to 8 weeks in spring with average temperatures maintained around 15° C. (60° F.).

*Growth rate*.—Vigorous, 6 to 8 blooming sized shoots are produced per one-gallon container in less than 1 year.

Foliage description:

*Leaf shape*.—Linear.

*Leaf division*.—Simple.

*Leaf base*.—Truncate and sheathed to base of shoot.

*Leaf apex*.—Narrowly acuminate.

*Leaf aspect*.—Sulcate, leaves initially emerge upright, then upright to slightly cascading.

*Leaf venation*.—Parallel, the midrib is raised on the lower surface, not prominent or conspicuous, color matches leaf color.

*Leaf margins*.—Entire, scabrous.

*Leaf attachment and arrangement*.—Sessile, arise in rosette-like.

*Leaf size*.—Average of 1 cm in width (at midpoint) and up to 80 cm in length when mature.

*Leaf number*.—Average of 30 per clump (shoot).

*Leaf surface*.—Upper and lower surfaces of mature leaves are dull and slightly rough to the touch, upper and lower surfaces of young leaves are smooth and glossy.

*Leaf color*.—Newly emerging leaves upper and lower surfaces: N144B becoming 154D at base, mature leaves upper and lower surface; 137A.

Flower description:

*Inflorescence type*.—Dense racemes of single flowers held on erect and strong scapes.

*Inflorescence size*.—Reaches an average of 16 cm in height and about 4 cm in width.

*Flower fragrance*.—Slight.

*Flower quantity*.—An average of 130 flowers per raceme, average of 1 raceme per clump.

*Flower lastingness*.—Flowers open from base towards the apex, average of 5 days per flower, not persistent, inflorescences lasts about 2 weeks.

*Flower buds*.—Oblong-obovate in shape, average of 3 mm in diameter and 2.2 cm in length, emerge 144C in color and mature to 5A.

*Flower aspect*.—Held horizontally then slightly downward at about a 45° angle as they mature, and vertical as they fade.

*Flower shape*.—Narrowly campanulate-tubular.

*Flower size*.—About 2.8 cm in length and 6 mm in diameter, flowers tend to be shorter in the heat of the summer.

*Tepals*.—5, fused into tube 2.2 cm in length and 6 mm in diameter with triangular-shaped free apex portion; about 3 mm in width and 2 mm in length, entire margin, broadly acute apex, inner and lower surface is glabrous and waxy, color when opening outer and inner surface; a blend of 1B and 5A, color when fully open outer and inner surface; 5A, color fades to 162B and then 162A.

*Peduncles* (*flowering stems*).—Reaching up to 76 cm in length (from base of plant to top of raceme) and an average of 1 cm in width, held erect, strong, color is a blend of 138A mid section to base and 144B at the mid section to top, surface is glabrous and slightly glaucous.

*Pedicels*.—Average of 1.5 mm in length and 1 mm in width, 191A in color, surface is glabrous and waxy.

Reproductive organs:

*Gynoecium*.—1 Pistil, about 2 cm in length and <1 mm in width, stigma is crested, minute and 145C in color, style is about 2 cm in length and 145C in color, ovary is superior, oblong-elliptic in shape, about 2.5 mm in length and 1.5 mm in width and 144A in color.

*Androcoecium*.—5 stamens, anthers are oblong in shape, dorsifixed, about 1.5 mm in length and 1 mm width and 162C in color, filaments are about 2 cm in length, <1 mm in width and 145C in color, pollen is moderate to abundant in quantity and 13A in color.

*Fruit and seed*.—Capsules; produced more abundantly when grown outdoors, ovoid-globose in shape, 3-parted, about 9 mm in length and 8 mm in width, a blend of 144A and 147A in color maturing to a blend of N200A, N200B, and 199A on the outer surface and 199B on the inner surface, glaucous surface becoming woody when mature, seeds; 3 per capsule, 3.5 to 4 mm in length, 200A in color.

It is claimed:

1. A new and distinct cultivar of *Kniphofia* plant named 'Echo Yello' as herein illustrated and described.

* * * * *